(12) United States Patent
El-Ghannam

(10) Patent No.: US 11,285,242 B1
(45) Date of Patent: Mar. 29, 2022

(54) PROCESSING AND BIOACTIVATION OF A NOVEL SIC MEDICAL DEVICE

(71) Applicant: The University of North Carolina at Charlotte, Charlotte, NC (US)

(72) Inventor: Ahmed El-Ghannam, Charlotte, NC (US)

(73) Assignee: THE UNIVERSITY OF NORTH CAROLINA AT CHARLOTTE, Charlotte, NC (US)

( * ) Notice: Subject to any disclaimer, the term of this patent is extended or adjusted under 35 U.S.C. 154(b) by 0 days.

(21) Appl. No.: 17/124,545

(22) Filed: Dec. 17, 2020

Related U.S. Application Data

(60) Provisional application No. 62/951,152, filed on Dec. 20, 2019.

(51) Int. Cl.
| | | |
|---|---|---|
| *A61L 27/08* | (2006.01) | |
| *B33Y 10/00* | (2015.01) | |
| *B29C 64/165* | (2017.01) | |
| *B33Y 70/10* | (2020.01) | |

(52) U.S. Cl.
CPC ............ *A61L 27/08* (2013.01); *B29C 64/165* (2017.08); *B33Y 10/00* (2014.12); *B33Y 70/10* (2020.01); *A61L 2420/02* (2013.01); *A61L 2430/02* (2013.01)

(58) Field of Classification Search
CPC ........ B33Y 10/00; A61L 27/08; B29C 64/165
See application file for complete search history.

(56) References Cited

U.S. PATENT DOCUMENTS

| | | | |
|---|---|---|---|
| 2,040,236 A | | 5/1936 | Benner et al. |
| 6,001,756 A | * | 12/1999 | Takahashi ............. C04B 35/575 501/90 |
| 2008/0057268 A1 | * | 3/2008 | Lu ......................... C04B 35/195 428/116 |
| 2009/0305017 A1 | | 12/2009 | His et al. |
| 2014/0206525 A1 | * | 7/2014 | Chaouki ............. C04B 38/0045 501/88 |
| 2018/0354860 A1 | * | 12/2018 | Wang ..................... C04B 35/111 |
| 2020/0385313 A1 | | 12/2020 | El-Ghannam et al. |
| 2021/0059787 A1 | * | 3/2021 | Levin .................. A61L 27/3633 |

FOREIGN PATENT DOCUMENTS

| | | | |
|---|---|---|---|
| CN | 104973873 A | | 10/2015 |
| CN | 106673662 A | * | 5/2017 |
| EP | 1728774 A1 | | 12/2006 |
| EP | 2138474 A1 | | 12/2009 |
| JP | 3368960 B2 | | 1/2003 |

OTHER PUBLICATIONS

Effect of processing parameters on the microstructure and mechanical behavior of a silicon carbide-silica composite. Procedia Manufacturing 34 (Jan. 2019) pp. 747-753 (Year: 2019).*

* cited by examiner

*Primary Examiner* — Cachet I Proctor
(74) *Attorney, Agent, or Firm* — Bradley C. Fach

(57) ABSTRACT

Silicon carbide (SiC) is an inert material with excellent biocompatibility properties. The biocompatibility is associated with the chemical inertness of the material. Tissue response to inert material is the formation of thin fibrous capsule. In some embodiments described herein, the conversion of SiC from inert material to bioactive material capable of stimulating cell function and making direct bond with tissue is described and the body response to bioactive materials is direct binding without any fibrous capsule.

4 Claims, 3 Drawing Sheets

PROCESSING AND BIOACTIVATION OF A NOVEL SIC MEDICAL DEVICE

CROSS REFERENCE TO RELATED APPLICATIONS

This application claims priority to, and the benefit of, U.S. provisional application No. 62/951,152, filed on Dec. 20, 2019, the entire contents of which are hereby incorporated by reference.

BACKGROUND OF THE INVENTION

Field of the Invention: Orthopedic surgery, Spine implant, Tissue engineering, bone banks, bone implants, maxillofacial surgery, and cosmetic surgery.

Porous scaffolds and spacers made of titanium alloy and poly[aryl-ether-ether-ketone] (PEEK) have been widely used in trauma and vertebrae surgeries. However, these metallic and polymeric implants do not promote osteoblast differentiation or bone tissue formation. The ultimate goal of using polymer or metal in orthopedic surgery is to fill the space (bone filling) while introducing minimal toxicity due to accumulation of metal ions (corrosion) or polymer degradation products.

Porous titanium implants possess a comparatively high stiffness which can lead to stress-shielding in the surrounding bone and subsequent implant loosening.[5] Additionally, titanium implants are subjected to in vivo corrosion and hydrogen embrittlement. An immune response to titanium alloy implants has been reported, where focal necrosis was seen in surrounding tissues near the stem of the implant. Atomic absorption spectroscopy of the digested tissue around the implant revealed the ratios of titanium, aluminum, and vanadium were similar to those in the alloy implant, suggesting the migration of metal debris due to wear from the head or stem and into the biological system. These wear particles can lead to titanium metallosis, a rare but potentially fatal condition where metal ions are released in the body, thereby inducing a variety of symptoms depending on the predominantly affected system. This is most notably marked by black synovial fluid in the affected area. Hemolytic anemia, surrounding tissue necrosis, fibrosis, and device loosening are all possible outcomes. Over the last 40 years, metallosis has occurred in an estimated 5% of patients receiving metal orthopedic implants.

To combat these issues, poly[aryl-ether-ether-ketone], commonly referred to as PEEK, has been used as an alternative implant, particularly for spinal implants. However, PEEK implants often experience poor osseointegration. A phenomenon termed the "PEEK-Halo" effect has been noted in CT imaging of PEEK vertebrae implants and is characterized by a "halo" made of fibrous tissue between the PEEK implant and the bone graft.[5] Given the current issues with traditional metallic and polymeric orthopedic implants, there is a need for a new design for medical device that can better serve trauma surgery patients.

Silicon carbide (SiC) has been widely utilized in high-temperature, high-power applications due to its high melting point, good thermal conductivity, and chemical inertness. As a biomaterial, SiC has been relatively unexplored, despite its good wear characteristics and resistance to corrosion. A 1998 study showed that SiC coated titanium alloy pins are biocompatible. In a separate study, it was shown that the interface between a SiC implant and rat femoral bone was morphologically similar to that of a bone-hydroxyapatite interface. Trials to incorporate SiC into a tissue engineering scaffold included the synthesis of a porous composite made of hydroxyapatite, alumina, and SiC. Human osteoblast like cells (Saos-2) seeded on the composite and cultured for one week had limited attachment and failed to spread on the material surface. Cell spreading is important marker for the biocompatibility of the material and is directly related to tissue integration. A separate study created SiC scaffold through the use of molten silicon and a wood-derived carbon template. Laser ablation was used in order to coat the SiC with bioactive glass to induce bioactivity. The bioactivity of the bioglass-coated SiC substrate was demonstrated by the presence of Ca and P on the material surface after immersion in simulated body fluid for 72 hours.

BRIEF SUMMARY OF THE INVENTION

Silicon carbide (SiC) is an inert material with excellent biocompatibility properties. The biocompatibility is associated with the chemical inertness of the material. Tissue response to inert material is the formation of thin fibrous capsule. In some embodiments, the present invention comprises the conversion of SiC from inert material to bioactive material for stimulating cell function and making direct bond with tissue. The body response to bioactive materials is directly bond without any fibrous capsule. The high chemical and mechanical stability of SiC poses manufacturing obstacles that make it difficult to process medical device or 3D SiC constructs. For example the application of high temperature (>2000 degrees C.) and pressure (1000-2000 atm) is required to fuse SiC particles into a 3D object. The application of high temperature and pressure to SiC particles creates a silicon oxide layer that bonds the particles together in a process called thermal oxidation. In some embodiments, the present invention uses NaOH chemical treatment to activate the surface of SiC and generate a silica gel layer that is able to polymerize and bond the SiC particles together at room temperature and without any compact pressure. The creation of the silica gel layer on the SiC surface transforms the surface to be bioactive. Bioactive materials have the ability to bond to bone, stimulate bone cell differentiation and enhance bone tissue formation. Subsequent thermal treatment, of the 3D object prepared by surface modified SiC, at moderate temperature (550-1000 C) can control the mechanical properties of the material. A porous scaffold made of surface modified SiC can be used as bone graft material, drug delivery system and cell delivery system. The rate of bone formation can be stimulated by adsorbing biological molecules that signal the stem cells and enhance osteoblast differentiation. Antibiotics can be adsorbed on the silica gel layer of SiC scaffold to treat and prevent infection. For trauma surgery, the SiC scaffold can serve as a spacer with osteogenic capabilities. The creation of the silica gel layer on the surface of SiC particles enables 3D printing using a water-based binder. During 3D printing, the water binder rehydrate the dried silica gel and enables bonding of the surface modified particles together.

DETAILED DESCRIPTION AND BEST MODE OF IMPLEMENTATION

Figure 1:
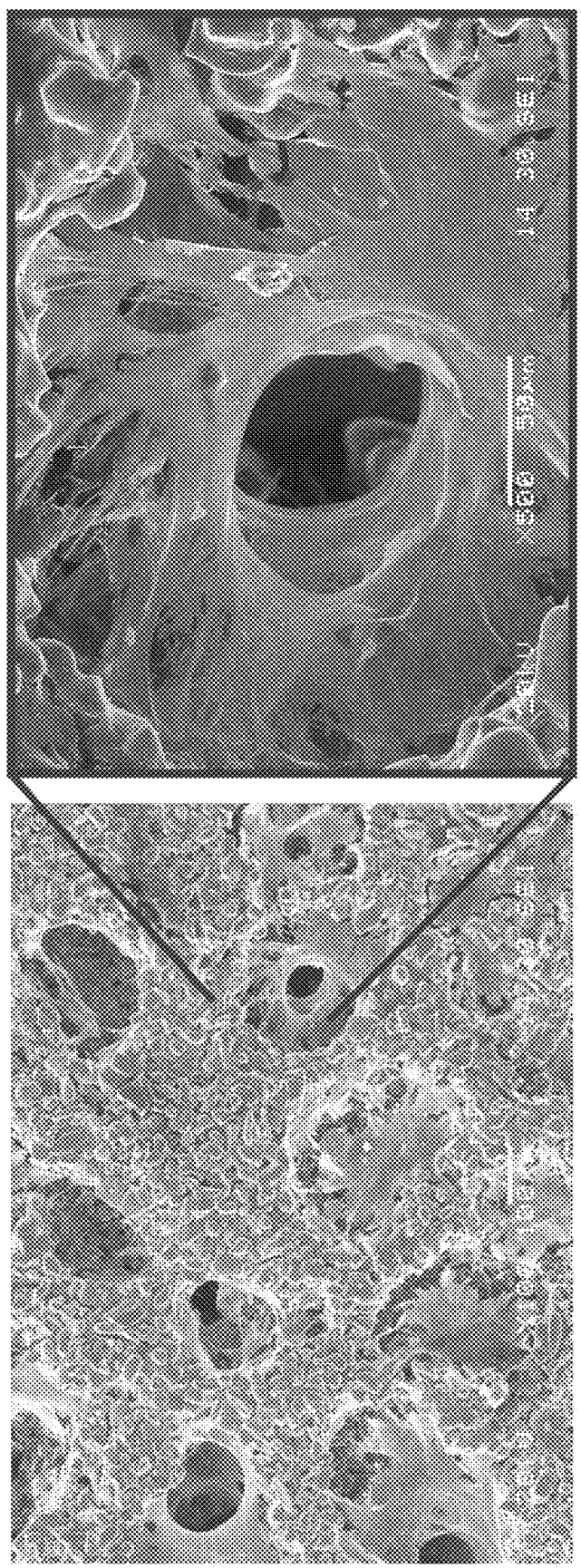
FIG. 1 shows SEM images of a) a 20% NaOH scaffold and b) a closeup of an MC3T3-E1 cell spread within a scaffold pore.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In some embodiments, the present invention uses NaOH to create silica gel layer on the surface of SiC at room temperature. The silica gel layer in a wet or dry format serves as a binder for the SiC particles at room temperature without a need for compact pressure. Therefore, SiC particles coated with dried silica gel layer can be used in a powder bed 3D printer to make using water as a binder. The spraying of water by the printer head will hydrate the dried silica gel layer coating the SiC particles. The hydrated silica gel enables bonding the SiC particles through hydrogen bonds and Si—O—Si bonds. After 3D printing, the dried scaffold can be subjected to thermal treatment to control porosity and mechanical strength. The porosity, mechanical properties and bioactivity of the SiC scaffold can be enhanced by thermal treatment in the temperature range 500-900 C in various atmospheres including oxygen, nitrogen and air. In some preferred embodiments, the thermal treatment of the 3D printed scaffold does not change the dimensions of the scaffold. This is because, the epitaxial growth of a crystalline silica nano wires that bridges the gap between the edges of the SiC particles.

Alternative method of preparing the surface modified bioactive scaffold is to use SiC particles coated with a wet silica gel layer. The SiC particles coated with the wet silica gel layer are placed in a mold of a specific shape. The compact pressure required to bring the particles in touch with each other can range from 0 to 0.1 MPa. Alternatively the compact pressure can be increased up to 250 MPa to make dense SiC object. The 3D scaffold can be removed from the mold, dried and subjected to heat treatment in a manner similar to what has been described above.

The surface modified scaffold prepared by either method as described above maintains a silica gel layer that can be reactivated in physiological solution and enables the bioactivity property of SiC. The bioactivity property allows the material to promote bone cell function, tissue formation and vascularization. The silica gel coating layer creates "negative" charge on the SiC surface that attracts calcium ions from physiological solution and enhance the deposition of a biomimetic hydroxyapatite layer similar to the mineral phase of bone. The biomimetic hydroxyapatite enhances protein adsorption and bone deposition by attached cells.

Ti alloy and PEEK do not form a biomimetic hydroxyapatite surface layer. Bioactive SiC is superior to Ti alloy and PEEK bone implants due to its ability to stimulate bone cells to produce bone and its ability to make direct bond with bone. Neither Ti alloy nor PEEK can stimulate bone cell function or bond to bone. Moreover, the release of silica dissolution product from the surface of bioactive SiC stimulates bone cell function, collagen type I formation, vascularization and inhibits osteoclast activities. In contrary, the release of metal ions from Ti alloy and the degradation products from PEEK have adverse effects on bone cells and bone formation.

The mechanical properties of surface-modified SiC is closer to that of bone. The mechanical properties can be controlled by the compact pressure of the modified SiC particles, the particle size, the percent silica phase created by the NaOH, and the porosity characteristics. The porosity can be further controlled by adding a scarifying agent like polyethylene glycol (PEG). For example, mixing surface modified SiC particles with 40% PEG and applying a compact pressure of 50 MPa was suitable to facilitate mechanical properties of the porous bioactive SiC scaffold similar to that of cancellous bone. A biomimetic calcium deficient carbonate containing hydroxyapatite layer was deposited on the material after 2 hours of immersion in simulated body fluid, indicating the osteoconductivity of the material and its ability to stimulate bone cell function and tissue formation. SEM, FTIR and molecular biology analyses demonstrated that cells attached to the surface of the bioactive SiC produced mineralized bone-like tissue with high osteocalcin concentration (FIG. 1).

The porous bioactive SiC scaffold has mechanical strength comparable to trabecular bone and can be used as a permanent bone substitute to treat large defects. The porosity characteristics and the stimulatory effects of the surface of bioactive SiC facilitated cell invasion, colonization and formation of mineralized bone matrix through the entire thickness of the porous SiC scaffold. The filling of the pores with the newly formed bone is expected to minimize the stress shielding effect. This is because the newly formed bone inside the pores of the scaffold is expected to remodel and have the same mechanical properties as natural bone. Bone formation inside porous titanium alloy or PEEK is difficult to form and often fibrous tissue is seen in the pores.

The porous bioactive SiC scaffold has mechanical strength comparable to trabecular bone and can be used as a permanent bone substitute to treat large defects.

The new approach to processing a porous SiC scaffold was to create a silica gel layer prior to thermal treatment to eliminate the need of high temperature treatment for SiC oxidation. Following NaOH treatment, plenty of silanol species: Si(OH)2, Si(OH)3, and Si(OH)4 are created on the SiC surface. These silanol groups are thermodynamically motivated to re-polymerize at room temperature to produce a hydrated SiO2 layer that bonds the SiC particles together. FTIR and SEM-EDX analyses provided evidence that as the NaOH concentration used for surface treatment increases, the silica gel layer increases. The area under the peak for the Si—OH band between 3740-2660 cm-1 showed over a 50-fold increase as the concentration of NaOH used increased from 10% to 40%. As the number of silanol groups increased on the SiC surface, these groups polymerize together and form Si—O—Si chains that bond the SiC particles together. FTIR analysis (FIG. 3) confirmed the increase in the area under the peak for the Si—O—Si band.

Subjecting the silica gel-bonded SiC to thermal treatment induced the transformation of the amorphous silica layer into a silica nanowires that bridged the interspace between the particles and provided further stabilization of the structure. XRD analysis showed that the crystalline silica phase is α-cristobalite.[13] SEM and FTIR analysis suggested that the silica nanowires grow by epitaxial growth of the silicate ions present in the silica gel layer. The growth of the (SiO2) crystals is enhanced by the presence of oxygen during heat treatment.[14, 15]

SiC has been widely utilized in high-temperature, high-power applications due to its high melting point, good thermal conductivity, and chemical inertness. As a biomaterial, SiC has been relatively unexplored, despite its good wear characteristics and resistance to corrosion. A 1998 study showed that SiC coated titanium alloy pins are biocompatible[16]. In a separate study, it was shown that the interface between a SiC implant and rat femoral bone was morphologically similar to that of a bone-hydroxyapatite interface[17]. Trials to incorporate SiC into a tissue engineering scaffold included the synthesis of a porous composite made of hydroxyapatite, alumina, and SiC. Human osteoblast like cells (Saos-2) seeded on the composite and cultured for one week had limited attachment and failed to spread on the material surface[18]. Cell spreading is important marker for the biocompatibility of the material and is directly related to tissue integration[19]. A separate study created SiC employing molten silicon and a wood-derived carbon template. Laser ablation was used in order to coat the SiC with bioactive glass to induce bioactivity. The bioactivity of the bioglass-coated SiC substrate was demonstrated by the presence of Ca and P on the material surface after immersion in simulated body fluid for 72 hrs.

A major challenge in creating a porous SiC scaffold is the high chemical inertness of the ceramic material due to the strong Si—C covalent bond. Sintering can be achieved by isostatic hot press at elevated temperature (>2000° C.) and pressure which is difficult to use on a commercial scale. An alternative approach is to use thermal oxidation, in the temperature range 1100-2000 degrees C., to bind SiC particles together with a thin layer of silicon oxide. The use of high temperature during thermal oxidation results in the formation of closed pores that hinders oxygen diffusion into the bulk of the SiC construct and compromise the mechanical properties. She et al. studies the effect of particle size and temperature on the formation of silicon oxide binder and reported that at high temperature, the volume percent of silica binder decreased with increasing the temperature due to the formation of closed pores. As the pores closed, the oxygen diffusion required for the creation of SiO2 binder is prohibited. Furthermore, it was found that, the silica glass layer that forms on the SiC particles has high resistance to oxidation and therefore prohibited further increase in the mechanical strength. Efforts to increase the mechanical strength included the use of aluminum oxide (Al2O3) and graphite powders[23]. Graphite addition was in the range of 25-60 volume % in order to increases the openness of the pores which facilitates the formation of silicon oxide as well as provides an initial structural support to the 3D SiC construct. The role of aluminum oxide was to react with the silicon oxide to form mullite (3Al2O3.2SiO2) above 1450 degrees C., which is expected to strengthen the mechanical properties. However, the authors reported lower mechanical properties for the mullite-bonded SiC ceramic compared to that of the SiC prepared by thermal oxidation. The porosity and flexural strength of porous SiC prepared with thermal oxidation at 1100° C./1 hr was 36.9% and 48 MPa, respectively[24]. On the other hand porous SiC prepared with graphite-mullite bonding method at (1450° C.) resulted in a porous SiC samples with 36.4% porosity, and flexural strength of 39.6 MPa[23]. The decrease in the mechanical strength in the mullite-bonded SiC samples is most probably attributed to the early oxidation of the graphite. Since graphite has been added in large quantity and its oxidation begins at 600° C., while the formation of silica on the surface of SiC starts at 750° C., the early oxidation of graphite prior to the silica formation can result in the loss of the structural support and compromise the mechanical integrity of the porous material. A report from a different research group showed that porous mullite-bonded SiC prepared at 1510° C. has 43.4% porosity, average pore size 8.3 µm, and a flexural strength in the range 5.1-24 MPa after heat treatment at 1450-1550 degrees C., respectively. The low mechanical strength could be attributed to the relatively larger SiC particle size (20 microns) used in the later study compared with the small particle size (2.3 microns) used by She et al.[23]. Taken all together, the formation of a silica layer prohibits further oxidation and limits the mechanical properties of SiC. Moreover, the use of graphite in large quantities (25-60%) to open the porosity and the use of aluminum oxide to form mullite at high temperature to bond the SiC particles closes the pores to just a few microns. Therefore, these methods are not suitable to form a porous tissue engineering scaffold with large interconnected open pores that facilitate cell ingrowth and vascularization. Moreover, the release of alumina ions has been shown to have an inhibitory effect on bone cell differentiation[25, 26].

Figure 2:
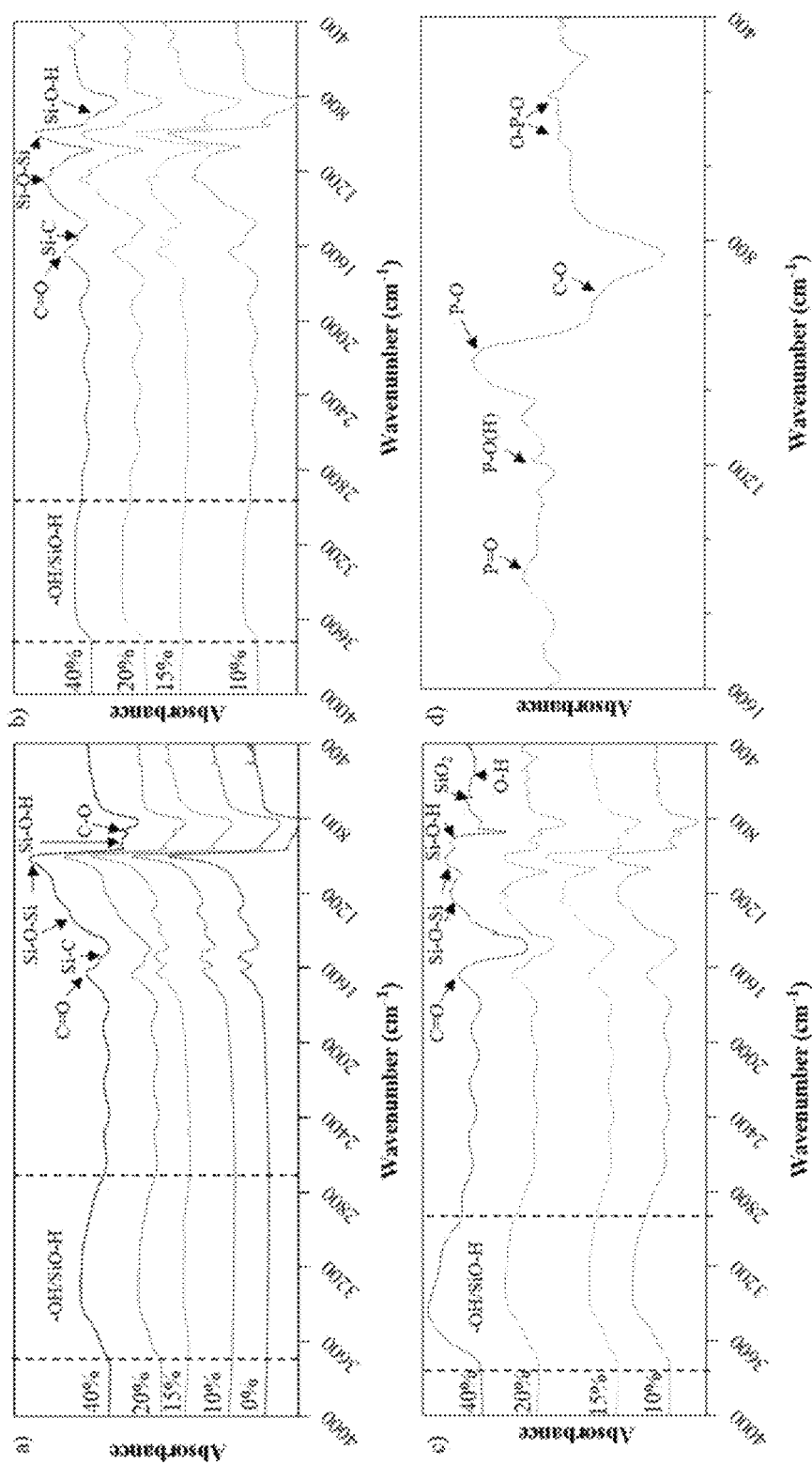
FIG. 2 presents FTIR spectra for a) control SiC powder, 10%, 15%, 20%, and 40% NaOH treated SiC after mixing. b) 10%, 15%, 201%, and 40% NaOH treated SiC after heat treatment. c) 10%, 15%, 20%, and 40% NaOH treated SiC after a 10-hour NaOH immersion. d) 10%, 15%, 20%, and 40% NaOH treated SiC after SBF immersion for 48 hours.
Figure 3:
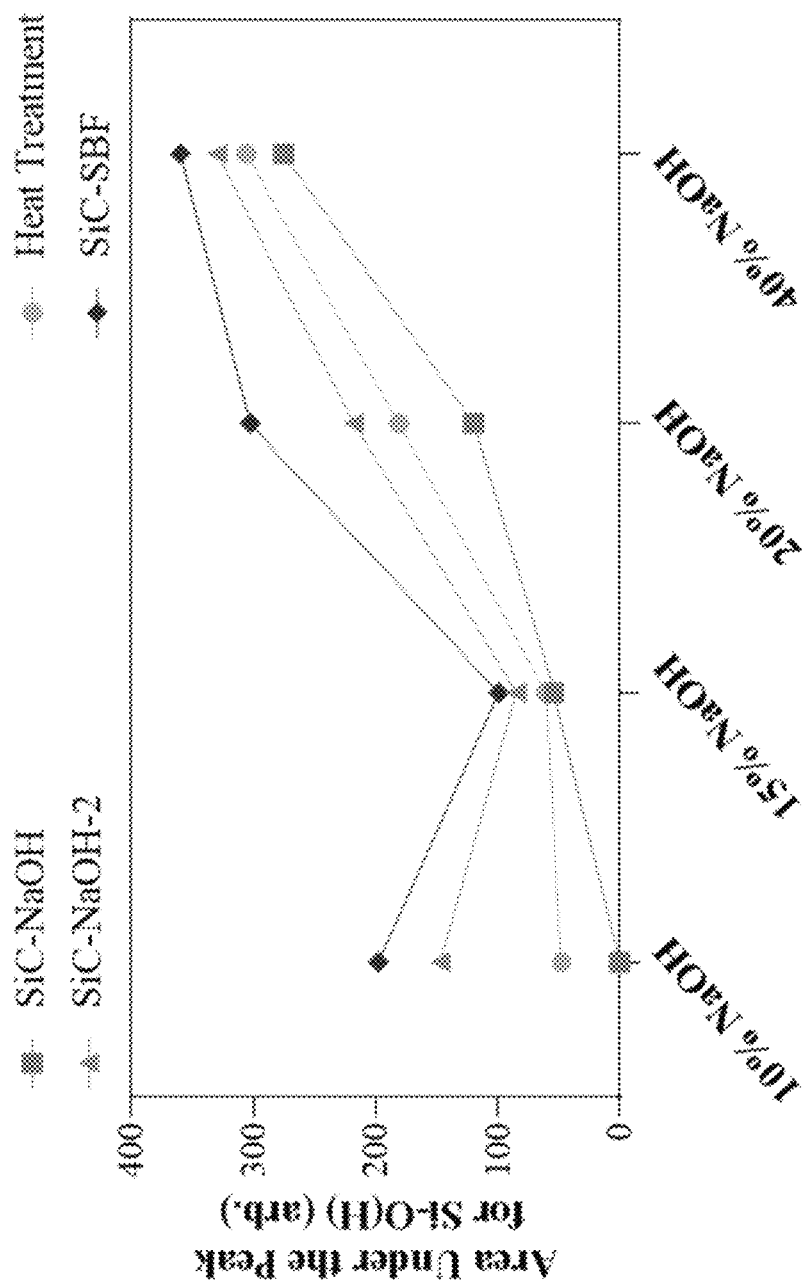
FIG. 3 displays Area under the curve for the Si—(O)H bands formed on the SiC surface treated with various concentrations of NaOH after mixing with NaOH (SiC—NaOH), heat treatment up to 900° C. (Heat Treatment), 10 hour NaOH immersion (SiC—NaOH-2), and after 48 hour SBF Immersion (SiC—SBF).

Our approach to processing a porous SiC scaffold was to create a silica gel layer prior to thermal treatment to eliminate the need of high temperature treatment for SiC oxidation. Following NaOH treatment plenty of silanol species: Si(OH)2, Si(OH)3, and Si(OH)4 are created on the SiC surface. These silanol groups are thermodynamically motivated to re-polymerize at room temperature to produce a hydrated SiO2 layer that bonds the SiC particles together. FTIR and SEM-EDX analyses provided evidences that as the NaOH concentration used for surface treatment increases the silica gel layer increases. The area under the peak for the Si—OH IR band at 900 cm-1 showed 100 folds increase as the NaOH increased from 2 to 40% (FIG. 3). As the number of silanol groups increased on the SiC surface, these groups polymerize together and form Si—O—Si chains that bond the SiC particles together. FTIR analysis (FIG. 2) confirmed the increase in the area under the peak for the Si—O—Si band.

Subjecting the silica gel-bonded SiC to thermal treatment induced the transformation of the amorphous silica layer into a silica nanowires that bridged the interspace between the particles and provided further stabilization of the structure. X-ray diffraction analysis demonstrated that the silica nano wires are made of cristobalite [El-Ghannam patent UNCC 2018]. SEM and FTIR analysis suggested that the silica nanowires grow by epitaxial growth of the silicate ions present in the silica gel layer. The growth of the SiO2 crystals is enhanced by the presence of oxygen during heat treatment. FTIR showed a sharp band at 980 cm-1 and broader band near 1200 cm-1 indicative of SiO2. The SEM-EDX demonstrated the growth of the silica nanowires perpendicular to the SiC surface. Moreover, the silica nanowires fuse together to form thick plates that bridge the particles giving the discs more strength. This new mechanism of sintering silicon carbide at low temperature and pressure is only possible due to the pre-creation of the silica gel layer by the NaOH treatment. Another advantage of the preformation of the silica gel binder is the stabilization of the porous structure of SiC during burning of the PEG at 350 degrees C.

REFERENCES INCORPORATED HEREIN BY REFERENCE

1. Lethaus B, Safi Y, ter Laak-Poort M, Kloss-Brandstatter A, Banki F, Robbenmenke C, Steinseifer U, Kessler P. Cranioplasty with customized titanium and PEEK implants in a mechanical stress model. J Neurotrauma 2012; 29(6):1077-83.
2. Kurtz S M, Devine J N. PEEK biomaterials in trauma, orthopedic, and spinal implants. Biomaterials 2007; 28(32):4845-4869.
3. Wu S L, Liu X M, Yeung K W K, Liu C S, Yang X J. Biomimetic porous scaffolds for bone tissue engineering. Materials Science & Engineering R-Reports 2014; 80:1-36.
4. Chaudhari A, Braem A, Vleugels J, Martens J A, Naert I, Cardoso M V, Duyck J. Bone Tissue Response to Porous and Functionalized Titanium and Silica Based Coatings. Plos One 2011; 6(9).
5. Phan K, Hogan J A, Assem Y, Mobbs R J. PEEK-Halo effect in interbody fusion. J Clin Neurosci 2016; 24:138-40.
6. Najeeb S, Bds Z K, Bds S Z, Bds M S. Bioactivity and Osseointegration of PEEK Are Inferior to Those of Titanium: A Systematic Review. J Oral Implantol 2016; 42(6):512-516.
7. Oliveira C. A., Candelária I. S., Oliveira P. B., Figueiredo A., Caseiro-Alves F. Metallosis: A diagnosis not only in patients with metal-on-metal prostheses. European Journal of Radiology Open 2014; 2:3-6.
8. Santavirta S, Takagi M, Nordsletten L, Anttila A, Lappalainen R, Konttinen Y T. Biocompatibility of silicon carbide in colony formation test in vitro. A promising new ceramic MR implant coating material. Arch Orthop Trauma Surg 1998; 118(1-2):89-91.
9. Hashiguchi K, Hashimoto K. Mechanical and histological investigations on pressureless sintered SiC dental implants. Okajimas Folia Anat Jpn 1999; 75(6):281-96.
10. Saki M, Narbat M K, Samadikuchaksaraei A, Ghafouri H B, Gorjipour F. Biocompatibility Study of a Hydroxyapatite-Alumina and Silicon Carbide Composite Scaffold for Bone Tissue Engineering. Yakhteh 2009; 11(1):55-60.
11. El-Ghannam A R, Ducheyne P, Risbud M, Adams C S, Shapiro I M, Castner D, Golledge S, Composto R J. Model surfaces engineered with nanoscale roughness and RGD tripeptides promote osteoblast activity. J Biomed Mater Res A 2004; 68(4):615-27.
12. González P, Serra J, Liste S, Chiussi S, León B, Pérez-Amor M, Martínez-Fernández J, de Arenano-López A R, Varela-Feria F M. New biomorphic SiC ceramics coated with bioactive glass for biomedical applications. Biomaterials 2003; 24(26):4827-4832.
13. Beasock D, Stokes T M, El-Ghannam A, Schmitz T. Effect of processing parameters on the microstructure and mechanical behavior of a silicon carbide-silica composite. Procedia Manufacturing 2019; 34:747-753.
14. Fisher G, Seacrist M R, Standley R W. Silicon Crystal Growth and Wafer Technologies. Proceedings of the Ieee 2012; 100:1454-1474.
15. Borghesi A, Pivac B, Sassella A, Stella A. OXYGEN PRECIPITATION IN SILICON. Journal of Applied Physics 1995; 77(9):4169-4244.
16. Santavirta S, Takagi M, Nordsletten L, Anttila A, Lappalainen R, Konttinen Y T. Biocompatibility of silicon carbide in colony formation test in vitro. A promising new ceramic MR implant coating material. Archives of orthopaedic and trauma surgery. 1998; 118(1-2):89-91. Epub 1998/12/02. PubMed PMID: 9833115.
17. Hashiguchi K, Hashimoto K. Mechanical and histological investigations on pressureless sintered SiC dental implants. Okajimas Folia Anat Jpn. 1999; 75(6):281-96. Epub 1999/04/28. PubMed PMID: 10217946.
18. Saki M, Narbat M K, Samadikuchaksaraei A, Ghafouri H B, Gorjipour F. Biocompatibility Study of a Hydroxyapatite-Alumina and Silicon Carbide Composite Scaffold for Bone Tissue Engineering. Yakhteh. 2009; 11(1):55-60. PubMed PMID: WOS:000265172700009.
19. El-Ghannam A R, Ducheyne P, Risbud M, Adams C S, Shapiro I M, Castner D, Golledge S, Composto R J. Model surfaces engineered with nanoscale roughness and RGD tripeptides promote osteoblast activity. J Biomed Mater Res A. 2004; 68(4):615-27. Epub 2004/02/27. doi: 10.1002/jbm.a.20051. PubMed PMID: 14986317.
20. González P, Serra J, Liste S, Chiussi S, León B, Pérez-Amor M, Martinez-Fernández J, de Arenano-López A R, Varela-Feria F M. New biomorphic SiC ceramics coated with bioactive glass for biomedical applications. Biomaterials. 2003; 24(26):4827-32. doi: https://doi.org/10.1016/S0142-9612(03)00405-8.
21. Ding S Q, Zhu S M, Zeng Y P, Jiang D L. Fabrication of mullite-bonded porous silicon carbide ceramics by in situ reaction bonding. Journal of the European Ceramic Society. 2007; 27(4):2095-102. doi: 10.1016/j.jeurceramsoc.2006.06.003. PubMed PMID: WOS:000243669800024.
22. She J H, Deng Z Y, Daniel-Doni J, Ohji T. Oxidation bonding of porous silicon carbide ceramics. Journal of Materials Science. 2002; 37(17):3615-22. doi: 10.1023/a:1016596805717. PubMed PMID: WOS:000177048800009.
23. She J H, Yang J F, Kondo N, Ohji T, Kanzaki S, Deng Z Y. High-strength porous silicon carbide ceramics by an 24. Eom J H, Kim Y W, Song I H, Kim H D. Processing and properties of polysiloxane-derived porous silicon carbide ceramics using hollow microspheres as templates. Journal of the European Ceramic Society. 2008; 28(5):1029-35. doi: 10.1016/j.jeurceramsoc.2007.09.009. PubMed PMID: WOS:000253554200022.
25. Krewski D, Yokel R A, Nieboer E, Borchelt D, Cohen J, Harry J, Kacew S, Lindsay J, Mahfouz A M, Rondeau V. Human health risk assessment for aluminium, aluminium oxide, and aluminium hydroxide. Journal of toxicology and environmental health Part B, Critical reviews. 2007; 10 Suppl 1(Suppl 1):1-269. doi: 10.1080/10937400701597766. PubMed PMID: 18085482.
26. Sansone V, Pagani D, Melato M. The effects on bone cells of metal ions released from orthopaedic implants. A review. Clinical cases in mineral and bone metabolism: the official journal of the Italian Society of Osteoporosis, Mineral Metabolism, and Skeletal Diseases. 2013; 10(1): 34-40. Epub 2013/05/20. doi: 10.11138/ccmbm/2013.10.1.034. PubMed PMID: 23858309.
27. Fisher G, Seacrist M R, Standley R W. Silicon Crystal Growth and Wafer Technologies. Proc IEEE. 2012; 100: 1454-74. doi: 10.1109/jproc.2012.2189786. PubMed PMID: WOS:000309838000034.
28. Borghesi A, Pivac B, Sassella A, Stella A. OXYGEN PRECIPITATION IN SILICON. J Appl Phys. 1995; 77(9):4169-244. doi: 10.1063/1.359479. PubMed PMID: WOS:A1995QV47900001.
29. Khan A S, Khalid H, Sarfraz Z, Khan M, Iqbal J, Muhammad N, Fareed M A, Rehman I U. Vibrational spectroscopy of selective dental restorative materials. Applied Spectroscopy Reviews. 2017; 52(6):507-40. doi: 10.1080/05704928.2016.1244069. PubMed PMID: WOS:000403107000001.
30. Ojima J. Determining of crystalline silica in respirable dust samples by infrared spectrophotometry in the presence of interferences. Journal of occupational health. 2003; 45(2):94-103. Epub 2003/12/04. PubMed PMID: 14646300.
31. P. Launder B A. INFRARED ANALYSIS OF ORGANOSILICON COMPOUNDS: SPECTRA-STRUCTURE CORRELATIONS. Morrisville, Pa.: 2013.
32. Xue S H, Xie H, Ping H, Li Q C, Su B L, Fu Z Y. Induced transformation of amorphous silica to cristobalite on bacterial surfaces. Rsc Advances. 2015; 5(88):71844-8. doi: 10.1039/c5ra13619a. PubMed PMID: WOS: 000360529900042.
33. Yin K, Lin H Y, Cai Q, Zhao Y, Lee S T, Hu F, Shao M W. Silicon nanowires nanogenerator based on the piezoelectricity of alpha-quartz. Nanoscale. 2013; 5(24): 12330-4. doi: 10.1039/c3nr03838f. PubMed PMID: WOS:000327507900041.

What is claimed is:

1. A SiC scaffold wherein the SiC scaffold is made by the following process:
   using NaOH to create a silica gel layer on a surface of SiC particles;
   spraying water from a printer head onto the silica gel layer to coat the SiC particles; and
   thermally treating the SiC to about 500 to 900 degrees Celsius.

2. The SiC scaffold of claim 1, wherein the silica gel layer is dried prior to the spraying of water from the printer head, the water rehydrating the gel layer.

3. The SiC scaffold of claim 1, wherein the SiC scaffold has a porosity.

4. The SiC scaffold of claim 3, wherein the SiC scaffold is bioactive and exhibits osteoconductivity.

* * * * *